(12) United States Patent
Walters et al.

US011467618B2

(10) Patent No.: US 11,467,618 B2
(45) Date of Patent: *Oct. 11, 2022

(54) FOOT PEDAL APPARATUS FOR USE WITH A WORKSTATION CONTROLLING A ROBOTIC SURGERY SYSTEM

(71) Applicant: Titan Medical Inc., Toronto (CA)

(72) Inventors: Chad C. Walters, Apex, NC (US); Kyle R. Millard, Youngsville, NC (US); Perry A. Genova, Chapel Hill, NC (US)

(73) Assignee: Titan Medical Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/193,262

(22) Filed: Mar. 5, 2021

(65) Prior Publication Data

US 2021/0191447 A1 Jun. 24, 2021

Related U.S. Application Data

(63) Continuation of application No. 15/846,986, filed on Dec. 19, 2017, now Pat. No. 10,969,817.

(51) Int. Cl.
*G05G 1/36* (2008.04)
*A61B 34/30* (2016.01)
(Continued)

(52) U.S. Cl.
CPC ............... *G05G 1/36* (2013.01); *A61B 34/30* (2016.02); *A61B 90/03* (2016.02); *G05G 1/01* (2013.01);
(Continued)

(58) Field of Classification Search
CPC .......... G05G 1/506; G05G 1/503; G05G 1/50; G05G 1/36; G05G 1/34; G05G 1/30;
(Continued)

(56) References Cited

U.S. PATENT DOCUMENTS 5,889,510 A 3/1999 Klarlund
8,120,301 B2 2/2012 Goldberg et al.
(Continued)

FOREIGN PATENT DOCUMENTS

DE 29 41 345 A1 4/1981
EP 2 545 856 1/2013
WO WO 1994/10962 5/1994

OTHER PUBLICATIONS

Search report dated Jun. 5, 2019 in European Patent Application No. 18213627.5 (in 9 pages).
(Continued)

*Primary Examiner* — Daniel D Yabut
(74) *Attorney, Agent, or Firm* — Knobbe Martens Olson & Bear, LLP

(57) ABSTRACT

A foot pedal apparatus for use with a workstation operated by a seated user in controlling a robotic surgery system is disclosed. In some embodiments, the apparatus includes a platform mountable to the workstation proximate a floor surface on which the workstation is located. The apparatus also includes a first pedal mounted on the platform and having an upwardly disposed actuation surface, and a second pedal mounted vertically elevated with respect to the first pedal and having an upwardly disposed actuation surface, the second pedal having at least a proximate portion vertically overlapping a distal portion of the first pedal such that the first and second pedals have a mounted depth in a direction away from the user that is less than a sum of the respective individual depths of the first and second pedals.

26 Claims, 5 Drawing Sheets

(51) Int. Cl.
*A61B 90/00* (2016.01)
*G05G 13/00* (2006.01)
*A61B 17/00* (2006.01)
*G05G 1/01* (2008.04)
*A61B 34/00* (2016.01)
*G05G 1/30* (2008.04)

(52) U.S. Cl.
CPC .............. *G05G 13/00* (2013.01); *A61B 34/76* (2016.02); *A61B 2017/00199* (2013.01); *A61B 2017/00973* (2013.01); *G05G 1/30* (2013.01)

(58) Field of Classification Search
CPC .... G05G 13/00; G10C 3/26; Y10T 74/20894; Y10T 74/20888; A61B 2017/00973; A61B 90/03; A61B 34/30
See application file for complete search history.

(56) References Cited

U.S. PATENT DOCUMENTS

| | | | |
|---|---|---|---|
| 8,423,182 | B2 | 4/2013 | Robinson et al. |
| 9,301,811 | B2 | 4/2016 | Goldberg et al. |
| 10,969,817 | B2 * | 4/2021 | Walters .................. G05G 13/00 |
| 2005/0103607 | A1 | 5/2005 | Mezhinsky |
| 2006/0145540 | A1 | 7/2006 | Mezhinsky |
| 2010/0225209 | A1 | 9/2010 | Goldberg |
| 2018/0078034 | A1 * | 3/2018 | Savall .................... A61B 90/60 |
| 2019/0187741 | A1 | 6/2019 | Walters et al. |

OTHER PUBLICATIONS

U.S. Appl. No. 15/846,986, Foot Pedal Apparatus for Use With a Workstation Controlling a Robotic Surgery System, filed Dec. 19, 2017.

* cited by examiner

FOOT PEDAL APPARATUS FOR USE WITH A WORKSTATION CONTROLLING A ROBOTIC SURGERY SYSTEM

CROSS-REFERENCE TO RELATED APPLICATION

This application is a continuation of U.S. application Ser. No. 15/846,986, filed on Dec. 19, 2017. The entire disclosure of the above application is incorporated herein by reference.

BACKGROUND

1. Field

This disclosure relates generally to a workstation for controlling a surgical apparatus and more particularly to a foot pedal apparatus associated with the workstation.

2. Description of Related Art

In robotic systems, such as surgical robotic systems, a workstation console may be provided to control a remotely located instrument through user input provided to an input device on the console. The user may be required to operate the workstation console for an extended period of time, and the comfort of the user may thus be of concern since user fatigue may result. Some workstations, in addition to hand controls that are grasped and operated by the user, may include one or more foot pedals that when actuated cause various surgical operations to be effected.

SUMMARY

In accordance with some embodiments, there is provided a foot pedal apparatus for use with a workstation located on a floor surface and operated by a seated user in controlling a robotic surgery system. The apparatus includes a platform mountable to the workstation proximate the floor surface. The apparatus also includes a first pedal mounted on the platform and having an upwardly disposed actuation surface, and a second pedal mounted vertically elevated with respect to the first pedal and having an upwardly disposed actuation surface. The second pedal has at least a proximate portion vertically overlapping a distal portion of the first pedal such that the first and second pedals have a mounted depth in a direction away from the user that is less than a sum of the respective individual depths of the first and second pedals.

The second pedal may be oriented at an angle to the floor surface to facilitate engagement of the actuation surface by a forefoot portion of the user's foot while the user's heel is resting on the floor surface and acting as a pivot for movement of the user's foot.

The first pedal may be oriented at an angle to the floor surface and the vertical overlap between the proximate portion of the second pedal and the distal portion of the first pedal may be selected to prevent inadvertent engagement of the actuation surface of the first pedal while actuating the second pedal.

The vertical overlap between the proximate portion of the second pedal and the distal portion of the first pedal may be selected to cause the mounted depth of the first and second pedals to be about 200 mm.

The vertical overlap may be at least about 12 mm.

The actuation surface of the second pedal may be oriented at an angle of about 14° with respect to the floor surface.

The actuation surface of the first pedal may be oriented at an angle of about 7° with respect to the floor surface.

The platform may be pivotably mounted to the workstation at a pivot point on the platform proximally located with respect to the user, thereby facilitating tilting of the platform to increase the respective angles of the actuation surfaces of the first and second pedals with respect to the floor surface to facilitate ergonomic operation of the first and second pedals by the feet of a user seated in the chair and having a seat portion at a reclining angle, the increase in the angles of the actuation surfaces generally corresponding to the reclining angle of the seat portion of the chair.

The actuation surface of the second pedal may be oriented at an angle of about 14° with respect to the seat portion of the chair and the actuation surface of the first pedal may be oriented at an angle of about 7° with respect to the seat portion.

The workstation may include an input device and hand controllers operable to generate input signals, and the platform may be configured to attach to the workstation at a position forward of the user's hands when seated in a chair in front of the workstation and grasping the hand controllers to permit the user's feet to be extended away from the chair for ergonomic operation of the first and second pedals.

The platform may include a sliding mount for mounting to the workstation, the sliding mount being operable to facilitate positioning the first and second pedals in an ergonomic position in accordance with a user's preferences.

The apparatus may include at least one additional pedal mounted on the platform spaced apart from the first and second pedals, and the first and second pedals may be mounted on the platform for accessibility by one foot of the user while the at least one additional pedal is mounted on the platform for accessibility by the other foot of the user.

The apparatus may include a third pedal mounted on the platform and having an upwardly disposed actuation surface, the third pedal being adjacent to the first pedal and correspondingly oriented, and a fourth pedal mounted vertically elevated with respect to the third pedal and having an upwardly disposed actuation surface, the fourth pedal being adjacent to the second pedal and correspondingly oriented.

The first, second, third and fourth pedals may be mounted closely adjacent on the platform for accessibility by the same foot of the user.

The apparatus may further include a barrier disposed between the first and third pedals and a barrier disposed between the second and fourth pedals, the barriers each protruding above the actuation surfaces of the respective pedals.

Each of the first, second, third and fourth pedals, when actuated, may produce respective input signals for controlling the robotic surgery system.

The workstation may be supported on a wheeled base and the platform may be pivotably mounted to the workstation to facilitate raising the platform with respect to the floor surface when moving the workstation.

Other embodiments and features will become apparent to those ordinarily skilled in the art upon review of the following description of specific disclosed embodiments in conjunction with the accompanying figures.

BRIEF DESCRIPTION OF THE DRAWINGS

In drawings which illustrate disclosed embodiments.

DETAILED DESCRIPTION

Figure 1:
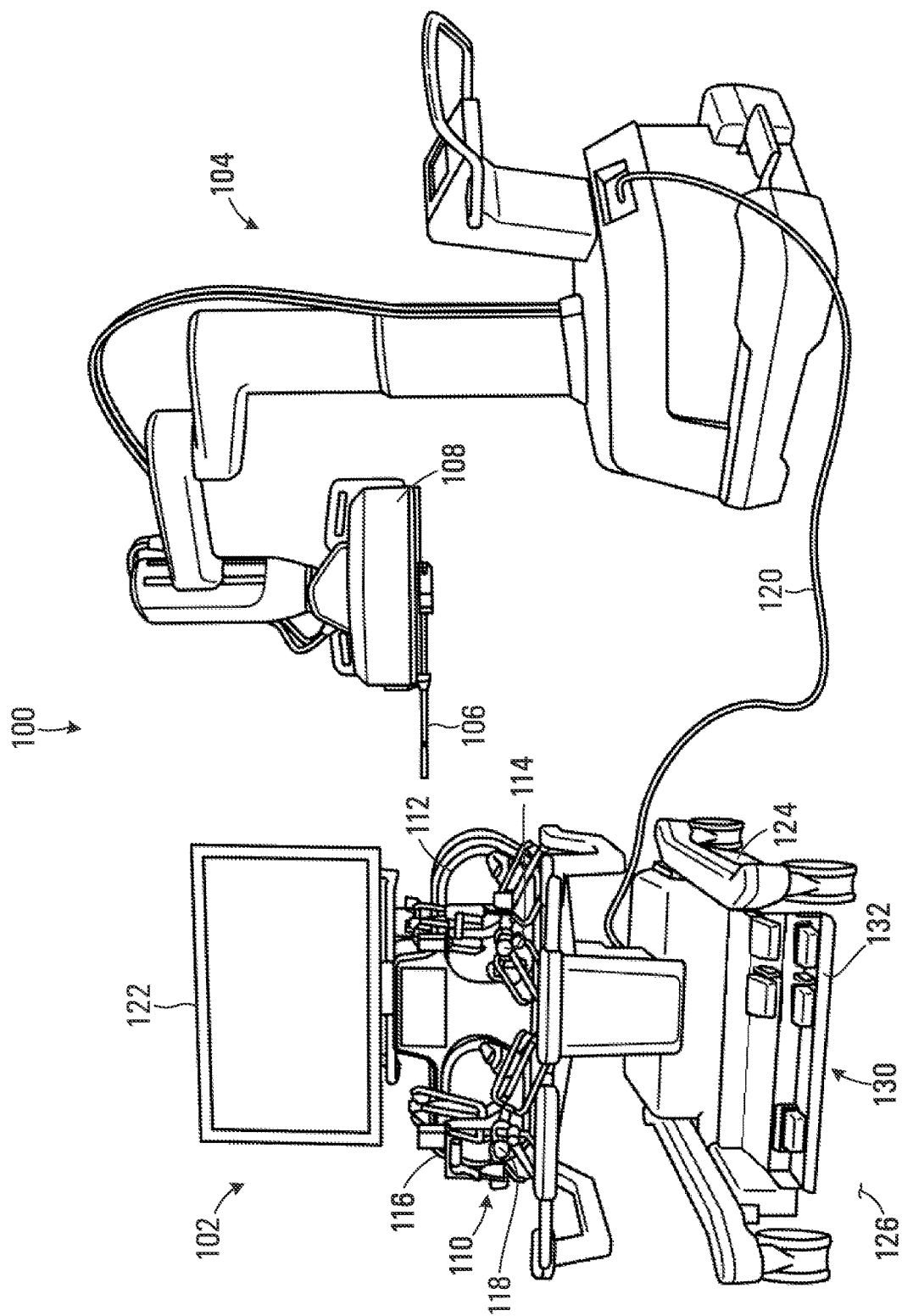
FIG. 1 is a perspective view of a robotic surgery system in accordance with some embodiments.

Referring to FIG. 1, a robotic surgery system is shown generally at 100. The robotic surgery system 100 includes a workstation 102 and a robotic surgery apparatus 104. The robotic surgery apparatus 104 includes at least one instrument 106 mounted on a moveable instrument mount 108 that houses an instrument drive (not shown) for manipulating the instrument. The workstation 102 includes an input device 110 for use by a user (generally a surgeon) for controlling the instrument 106 via the instrument drive to perform surgical operations on a patient. The input device 110 may be implemented using a haptic interface device available from Force Dimension, of Switzerland, for example. The input device 110 shown in FIG. 1 includes a right input device 112 having a right hand controller 114 and a left input device 116 having a left hand controller 118, the hand controllers being mechanically coupled to the respective input devices. In some embodiments the instrument 106 includes a right side instrument and a left side instrument (not shown) and movement of the right and left hand controllers 114 and 118 controls movements of the respective right and left instruments.

In this embodiment the workstation 102 is in communication with the robotic surgery apparatus 104 via an interface cable 120 for transmitting signals between the workstation and the instrument. Input signals are generated by the right and left input devices 112 and 116 in response to movement of the hand controllers 114 and 118 by the user and the instrument 106 is spatially positioned in response to the input signals.

The workstation 102 also includes a display 122 for displaying real time images and/or other graphical depictions of the surgical workspace produced by a camera (not shown) associated with the instrument 106. The display 122 may further be operable to provide other visual feedback and/or instructions to the user. The workstation 102 is supported on a wheeled base 124 permitting the workstation to be moved over a floor surface 126 for relocating the workstation. The workstation 102 further includes a foot pedal apparatus 130 having a platform 132 that is mounted to the workstation proximate the floor surface 126.

Figure 2:
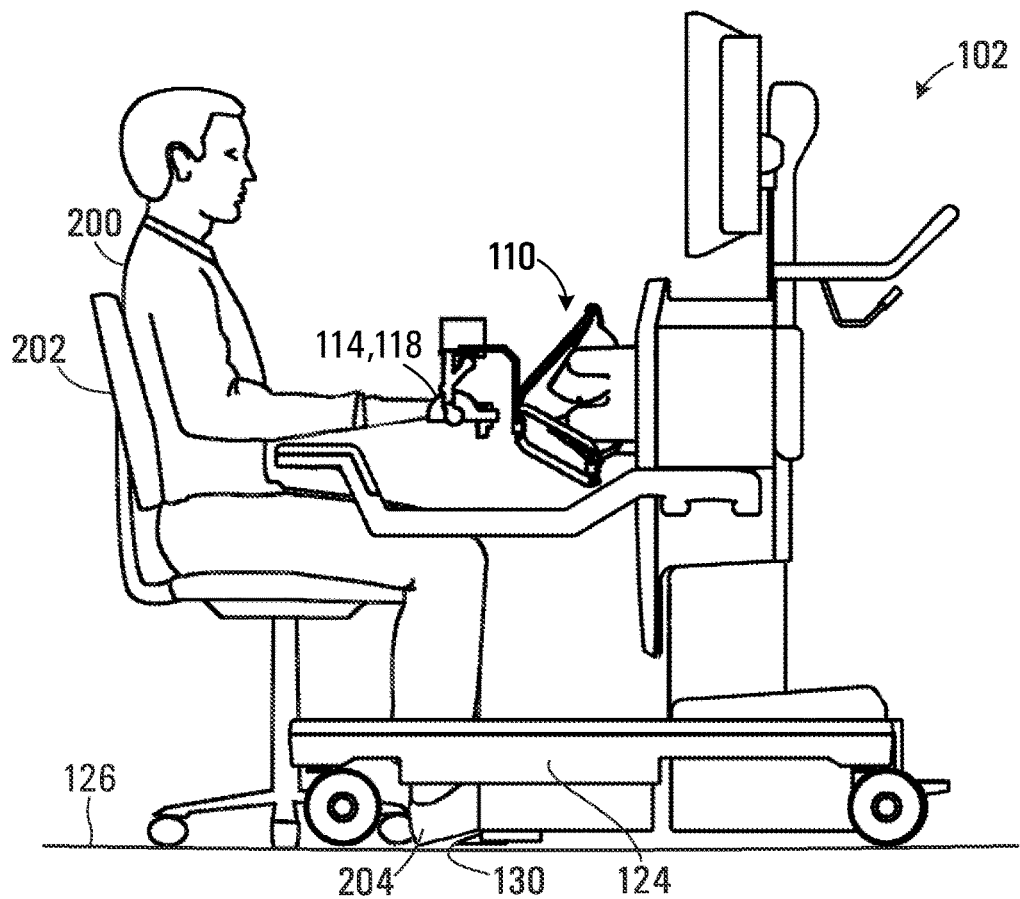
FIG. 2 is a side view of a workstation of the robotic surgery system shown in FIG. 1.

A side view of a user 200 seated in a chair 202 for operating the workstation 102 is shown in FIG. 2. Referring to FIG. 2, the user 200 grasps the hand controllers 114, 118 of the input device 110 and the user's right foot 204 is positioned to operate the foot pedal apparatus 130. In the embodiment shown, the foot pedal apparatus 130 is mounted to the workstation 102 at a position forward of the hands of the user 200 when seated in the chair 202 in front of the workstation and grasping the hand controllers 114, 118 causing the user's feet to be extended away from the chair for ergonomic operation of the workstation.

Figure 3:
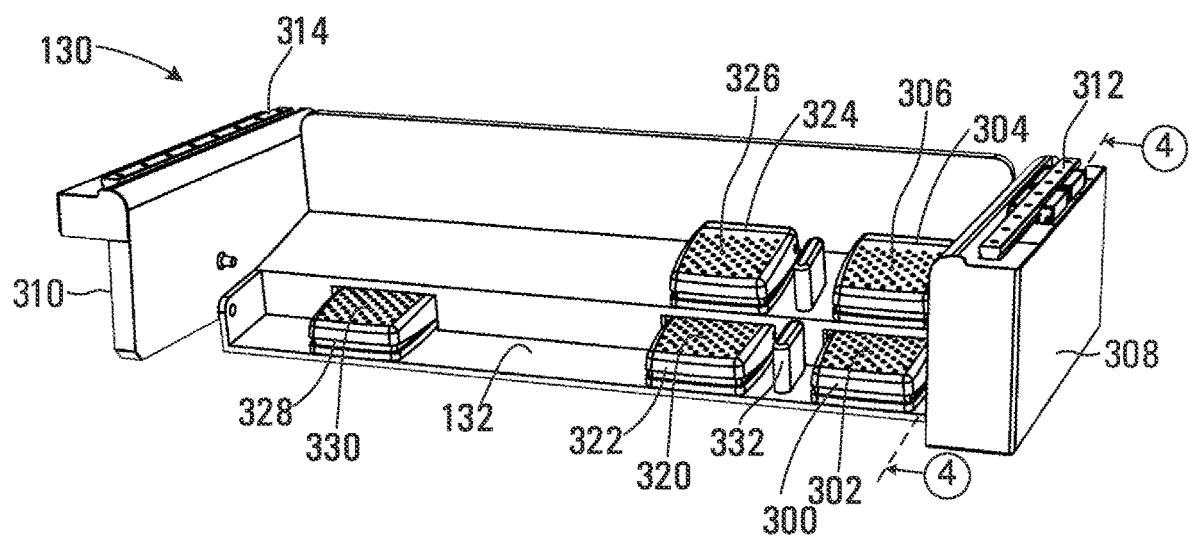
FIG. 3 is a perspective view of a foot pedal apparatus of the workstation shown in FIG. 2.
Figure 4:
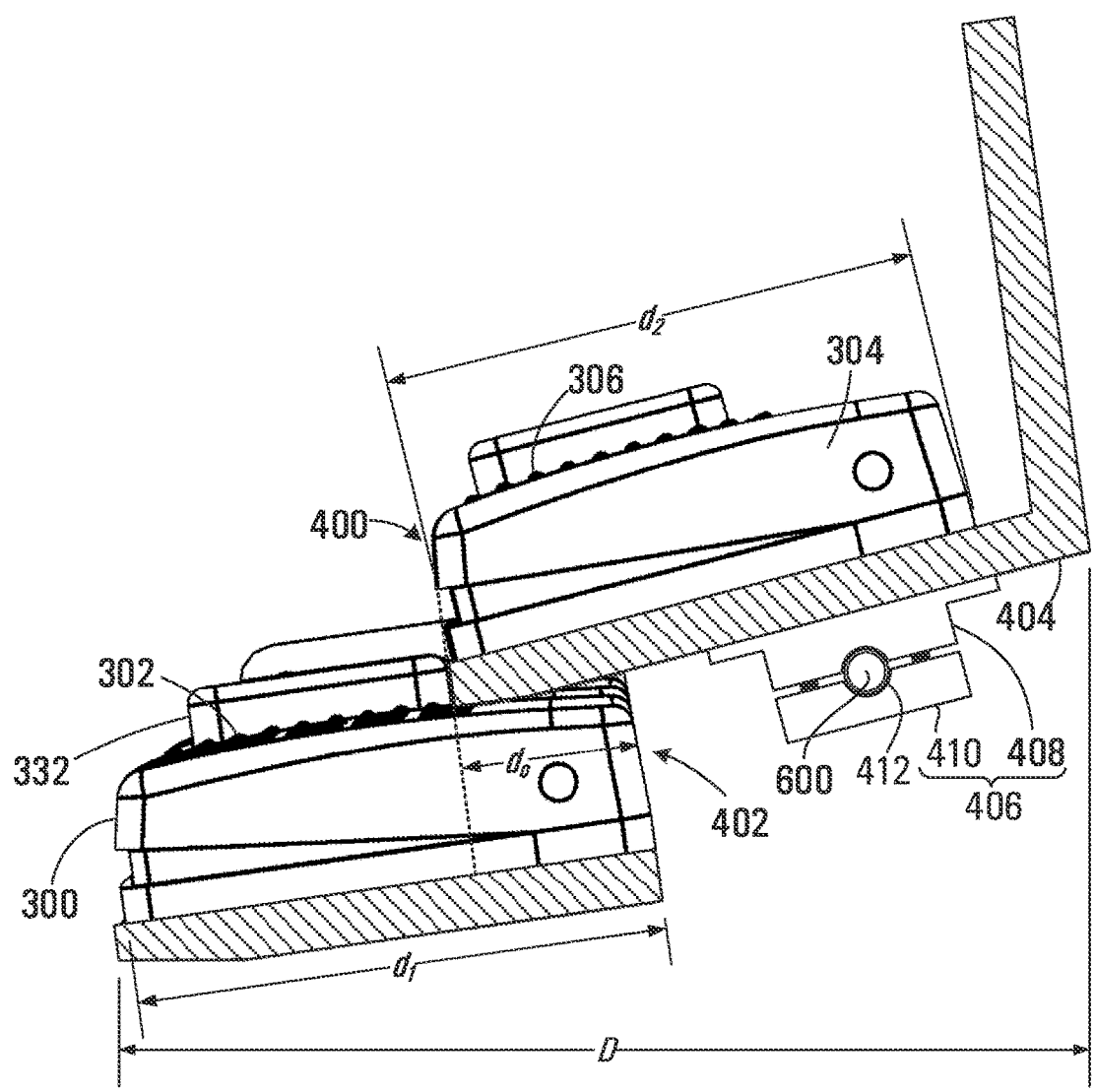
FIG. 4 is a cross sectional view of a platform portion of the foot pedal apparatus, taken along the lines 4-4 in FIG. 3.

The foot pedal apparatus 130 is shown in isolation in FIG. 3 and includes a first pedal 300 mounted on the platform 132 and having an upwardly disposed actuation surface 302. Referring to FIG. 3, the foot pedal apparatus 130 also includes a second pedal 304 mounted vertically elevated with respect to the first pedal 300 and having an upwardly disposed actuation surface 306. The platform 132 portion of the foot pedal apparatus 130 is shown in FIG. 4 in a cross sectional view taken along the lines 4-4 shown in FIG. 3. The second pedal 304 has at least a proximate portion 400 vertically overlapping a distal portion 402 of the first pedal 300. In the embodiment shown in FIG. 3 the degree of overlap is indicated by the overlap dimension $d_o$. The first and second pedals thus have a mounted depth D in a direction away from the user. The depth D is less than a sum of the respective individual depths $d_1$ and $d_2$ of the first and second pedals 300 and 304. In some embodiments the vertical overlap $d_o$ may be selected to cause the mounted depth D of the first and second pedals 300 and 304 to be about 200 mm. The overlap dimension $d_o$ may be about 12 mm or greater. The platform 132 shown in FIG. 3 is a tiered platform, but in other embodiments it may be otherwise configured for mounting of the first pedal 300 and second pedal 304.

Figure 5:
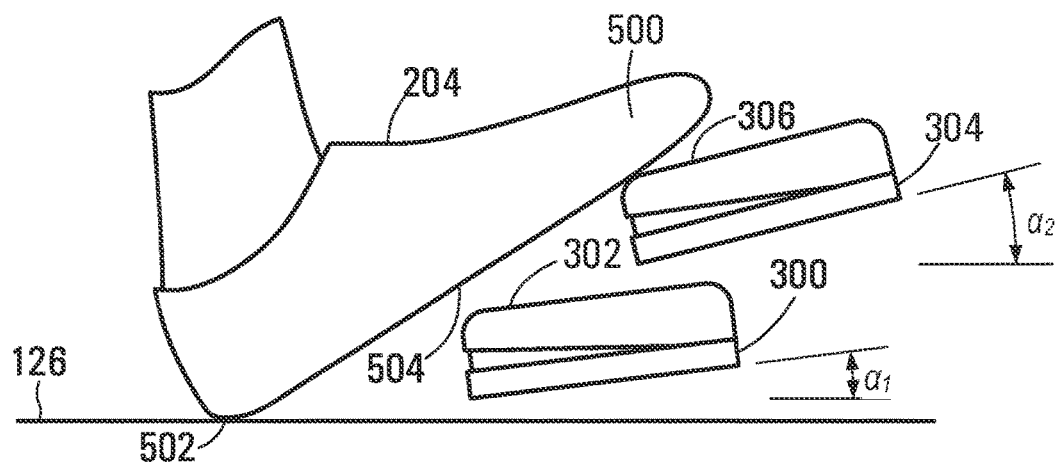
FIG. 5 is a schematic view of a user's foot and first and second pedals of the foot pedal apparatus shown in FIG. 3.

Engagement of the first and second pedals 300 and 304 by the foot 204 of the user 200 is depicted in schematic view in FIG. 5. Referring to FIG. 5, the first pedal 300 is oriented at an angle to the floor surface 126. In this embodiment the first pedal 300 is oriented at an angle $\alpha_1$ to the floor surface 126. The angle $\alpha_1$ is selected to facilitate engagement of the actuation surface 306 of the second pedal 304 by a forefoot portion 500 of the user's foot 204 while the user's heel 502 is resting on the floor surface and acting as a pivot for movement of the user's foot. In the embodiment shown in FIG. 5, the second pedal 304 is oriented at an angle $\alpha_2$ to the floor surface 126. The angles $\alpha_1$, $\alpha_2$ and the vertical overlap $d_o$ (shown in FIG. 4) are selected to prevent inadvertent engagement of the actuation surface 302 of the first pedal 300 while actuating the second pedal 304 with the forefoot portion 500 of the user's foot. As shown in FIG. 5, the pivoting of the user's foot 204 at the heel 502 in combination with the location and angles of the first and second pedals 300 and 304 place the actuation surface 302 of the first pedal below an arch portion 504 of the user's foot. In the embodiment shown in FIG. 5, the angle $\alpha_1$ may be about 7° with respect to the floor surface 126 and the angle $\alpha_2$ may be about 14° with respect to the floor surface.

As shown in FIG. 2, when the user 200 is seated in the chair 202 in front of the workstation 102 and the user's hands are grasping the left and right hand controllers 114 and 118, the user's feet will generally be extended away from the chair forward of the user's hands. This position facilitates ergonomic operation of the first and second pedals 300 and 304.

Referring back to FIG. 3, in the embodiment shown the foot pedal apparatus 130 includes a pair of slide mounts 308 and 310 having respective tracks 312 and 314. The platform 132 is attached between the slide mounts, which are in turn mounted via the respective tracks 312 and 314 to the wheeled base 124 (shown in FIG. 1 and FIG. 2). The slide mounting of the foot pedal apparatus 130 to the wheeled base 124 facilitates positioning of the platform 132 in accordance with the preferences of the user 200 to permit the user's feet to be extended away from the chair for ergonomic operation of the first and second pedals 300 and 304. The tracks 312 and 314 on the respective slide mounts 308 and 310 provide for adjustment of the foot pedal apparatus 130 toward or away from the user 200 to facilitate a variety of users of differing height and/or differing preferences.

Still referring to FIG. 3, in the embodiment shown the foot pedal apparatus 130 include additional pedals mounted on the platform 132. The foot pedal apparatus 130 includes a third pedal 320 mounted on the platform 132 and having an upwardly disposed actuation surface 322. The third pedal 320 is mounted adjacent to the first pedal 300 and has a corresponding orientation. The foot pedal apparatus 130 further includes a fourth pedal 324 mounted vertically elevated with respect to the third pedal 320 and having an upwardly disposed actuation surface 326 for actuation by the forefoot portion 500 of the user's foot. The fourth pedal 324 is adjacent to the second pedal 304 and correspondingly oriented.

In the embodiment shown the foot pedal apparatus 130 includes an additional fifth pedal 328 mounted on the platform 132 and having an upwardly disposed actuation surface 330. The fifth pedal 328 is spaced apart from the first, second, third and fourth pedals 300, 304, 320 and 324. In this embodiment, the first and second pedals 300 and 304 are mounted on the platform for accessibility by the right foot 204 of the user 200. The additional fifth pedal 328 is mounted on the platform 132 for accessibility by the other foot of the user 200. The third pedal 320 and fourth pedal 324 would generally be ergonomically accessible by the user 200 moving the same right foot 204 between the respective actuation surfaces of these adjacently located pedals. In the embodiment shown, the pedals are located closely adjacent on the platform 132 such that minimal side to side movement of the user's foot 204 is required for actuating either the left pedals 300, 304 or right pedals 320, 324. In the embodiment shown, the first pedal 300 and third pedal 320 are separated by a barrier 332, which protrudes slightly above the respective actuation surfaces 302 and 322 and acts to prevent the user's foot inadvertently actuating both pedals at once and acts as a haptic feedback to help position the user's foot without having to look away from the display 122. A similar barrier is included between the second pedal 304 and fourth pedal 324.

Each of the first, second, third, fourth, and fifth pedals 300, 304, 320, 324, and 328, when actuated, produce respective input signals, transmitted via the interface cable 120 to the robotic surgery apparatus 104 for controlling operation (FIG. 2). In embodiments where the instrument 106 includes left and right instruments, the pedals 300 and 304 may be associated with the right instrument and the pedals 320 and 324 may be associated with the left instrument.

Some instruments used in robotic surgery are configured to receive an electrical current to provide cutting and/or coagulation functions. The electrical current may be supplied by an electrosurgical unit (not shown) at radio frequencies (RF) and concentrated on tissue being manipulated by the instruments to cause coagulation of blood and/or cauterization of blood vessels in tissue at lower current density and parting of tissue at higher current density. In some embodiments the pedals 300 and 320 are configured to cause low current to be supplied to the respective right and left instruments for coagulation purposes while the upper pedals 304 and 324 are configured to cause high current to be supplied to the respective right and left instruments for cutting purposes. In electrosurgical cutting, tissue is parted through generation of high temperatures (typically in the region of 400° C.) that cause tissue to vaporize as the instrument is passed through the tissue. The electrosurgical cut requires only minimal force when compared to conventional scalpel or scissor cuts as it is the current that delivers the energy for performing the work of the cutting. The high temperatures also have the effect of sealing the incision by cauterizing vessels and causing coagulation of blood. Lower current density may result in temperatures high enough to cause coagulation and/or cauterization but insufficient to produce vaporization of tissue. Examples of instruments that may be accommodated by the instrument mount 108 include scissors, a Maryland dissector, and a hook cautery.

In the robotic surgery system embodiment shown in FIG. 1, the fifth pedal 328 acts as a clutch pedal configured to inhibit further movement of the instrument 106 when depressed by the foot of the user 200. When the fifth pedal 328 is depressed, the right and left hand controllers 114 and 118 are decoupled from the instrument 106. Further movement of the hand controllers therefore does not cause movement of the instrument 106 until the fifth pedal 328 is again released.

In other robotic surgery systems the foot pedal apparatus 130 may be differently configured and may have a fewer or greater number of pedals.

Figure 6:
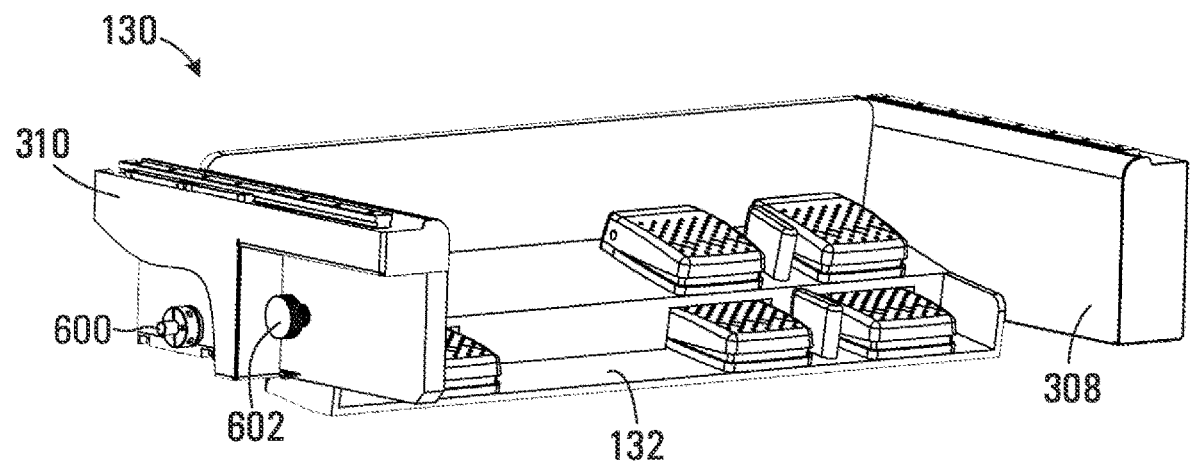
FIG. 6 is another perspective view of the foot pedal apparatus of the workstation shown in FIG. 2 in accordance with some embodiments.

The foot pedal apparatus 130 is shown in a left side perspective view in FIG. 6 with part of a cover of the slide mount 310 cut away. Referring to FIG. 6, in the embodiment shown, the platform 132 is pivotably mounted between the respective slide mounts 308 and 310 on a circular rod 600 to facilitate raising the platform with respect to the floor surface 126 when moving the workstation 102. The rod 600 extends between the slide mounts 308 and 310 and is able to rotate freely. In FIG. 6 the platform 132 is shown in a lowered position making the foot pedals accessible for operation. Referring back to FIG. 4, the platform 132 has a pair of pivots mounted to an underside 404 of the platform. One of the pivots is shown in FIG. 4 at 406. The pivot 406 has a base portion 408 mounted to the underside 404 of the platform 132 and also includes a clamp portion 410. The base portion 408 and clamp portion 410 are configured to provide an opening 412, which receives the rod 600 for mounting the platform 132 to the rod. The clamp portion 410 engages the rod 600 and facilitates a pivoting motion of the platform between the slide mounts 308 and 310.

Figure 7:
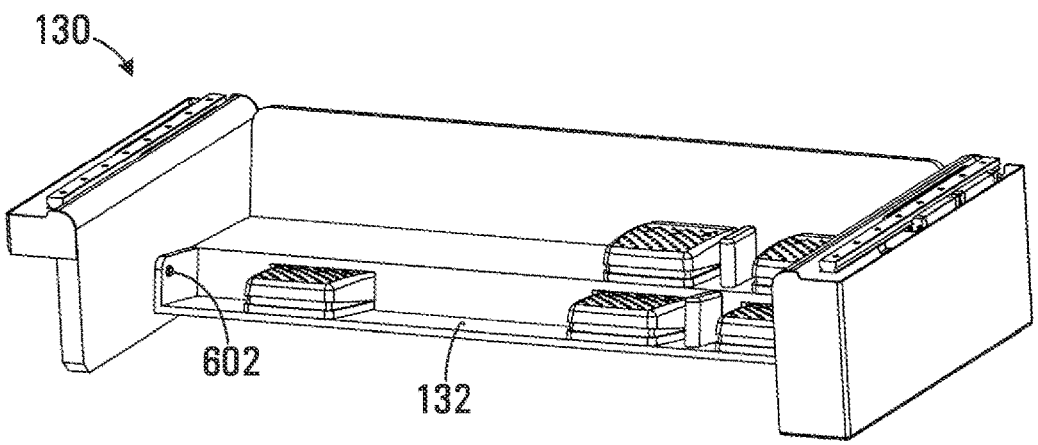
FIG. 7 is a perspective view of the foot pedal apparatus with the platform in a raised position according to some embodiments.

Referring to FIG. 6, the foot pedal apparatus 130 also includes a spring pin 602 that extends through the slide mount 310 and is configured to secure the platform 132 in the raised position. The foot pedal apparatus 130 is shown in FIG. 7 with the platform 132 in the raised position, the spring pin 602 engaging with an opening in the side of the platform to retain the platform in the raised position for transport of the workstation 102. When the spring pin 602 is disengaged, the platform 132 is able to pivot downwardly toward the floor surface 126 to make the pedals accessible for operation, as shown in FIG. 6.

Figure 8:
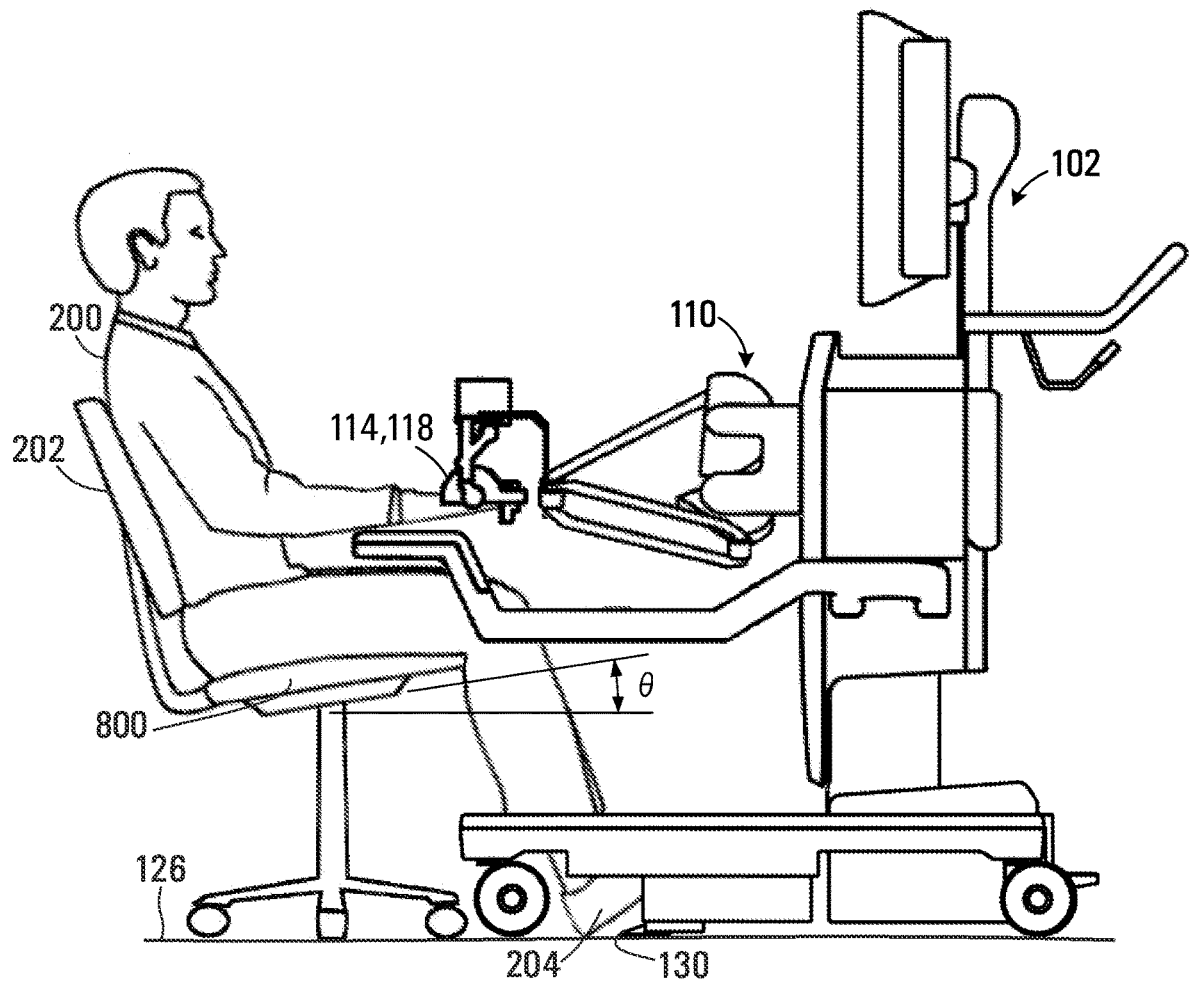
FIG. 8 is a side view of a workstation of the robotic surgery system shown in FIG. 1 in accordance with some embodiments.
Figure 9:
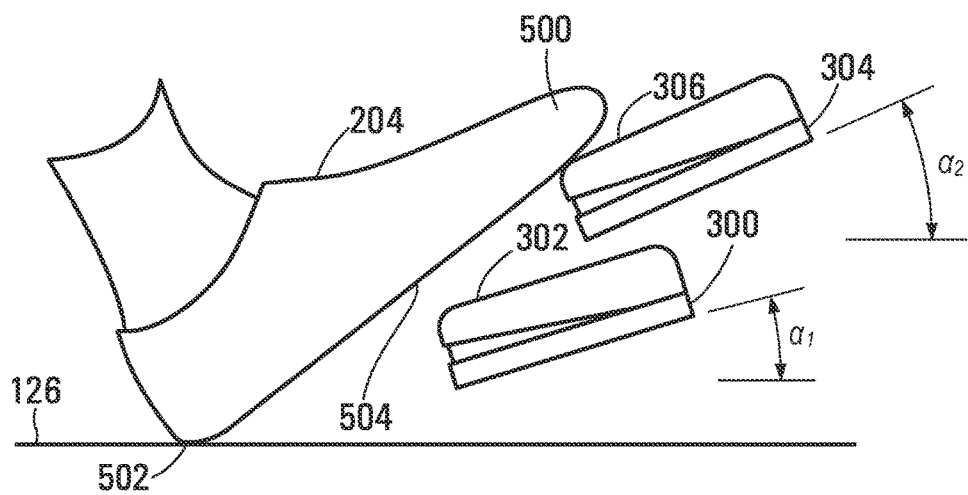
FIG. 9 is a schematic view of a user's foot and first and second pedals of the foot pedal apparatus shown in FIG. 3 for the workstation shown in FIG. 8 according to some embodiments.

Referring to FIG. 8, in some cases the user 200 may prefer a slightly reclining seated position where a seat portion 800 is disposed at a seat angle $\vartheta$ with respect to the floor surface 126. Under these reclining conditions, the engagement of the first and second pedals 300 and 304 by the foot 204 of the user 200 may be as depicted in schematic view in FIG. 8. The forefoot portion 500 of the user's foot 204 would naturally pivot upwardly about the heel 502, especially as the user extends the chair 202 away from the workstation 102 causing their legs to stretch out. The amount the user may extend the chair 202 away from the workstation console 102 would be dependent on the length of the user's arms and a reach of the input device 110. In this embodiment the first pedal 300 and second pedal 304 are configured to facilitate an increase in the angles $\alpha_1$ and $\alpha_2$ of the actuation surfaces 302 and 306 to facilitate ergonomic operation of the first and second pedals by the feet of the user 200 when seated in the chair 202 having the seat portion 800 at the reclining seat angle $\vartheta$. The increase in the angles $\alpha_1$ and $\alpha_2$ may generally correspond to the seat angle $\vartheta$. For example, in some embodiments the angles $\alpha_1$ and $\alpha_2$ may simply be increased by an amount corresponding to the seat angle $\vartheta$. In other embodiments the increase in the angles $\alpha_1$ and $\alpha_2$ may be in proportion to the seat angle $\vartheta$.

To facilitate changing the angles $\alpha_1$ and $\alpha_2$, the foot pedal apparatus 130 may be configured to permit pivoting about a proximal portion of the platform 132. For example, a pivot similar to the pivot 406 shown in FIG. 4 may be mounted at a proximal location on the platform 132 (i.e. below the first pedal 300 in FIG. 4) thus facilitating tilting of the platform to increase the respective angles of the actuation surfaces 302 and 306. In some embodiments the actuation surface 306 of the second pedal may be oriented at an angle of about 14° with respect to a seat portion of a chair for seating the user and the actuation surface 302 of the first pedal may be oriented at an angle of about 7° with respect to the seat portion.

The above disclosed embodiments provide a foot pedal apparatus for the workstation configured for ergonomic operation by the user in reducing the mounted depth of the apparatus which allows the foot pedals to be located in an optimal ergonomic position for the user. Further, the angle of the pedals facilitates comfortable operation for users in a variety of preferred seated positions. The angles of the pedals in combination with the mounted depth also prevent inadvertent actuation of a lower pedal when operating an upper pedal.

While specific embodiments have been described and illustrated, such embodiments should be considered illustrative of the disclosure only and not as limiting the disclosure as construed in accordance with the accompanying claims.

What is claimed is:

1. A foot pedal apparatus for use with a robotic surgery system workstation, the apparatus comprising:
    a first mount configured to be mounted to the workstation;
    a second mount configured to be mounted to the workstation;
    a pivotable platform extended between the first and second mounts, the pivotable platform being mounted on a rod extending between the first and second mounts;
    a first pedal mounted on the pivotable platform and including a first upwardly disposed actuation surface, the first actuation surface positioned at a first angle relative to a floor surface; and
    a second pedal mounted vertically elevated with respect to the first pedal and including a second upwardly disposed actuation surface, the second actuation surface positioned at a second angle relative to the floor surface, the second pedal including at least a proximal portion overlapping a distal portion of the first pedal,
    wherein the pivotable platform is configured to pivot and alter at least one of the first angle of the first actuation surface or the second angle of the second actuation surface relative to the floor surface to facilitate ergonomic operation of the first and second pedals,
    wherein the pivotable platform is configured to pivot on the rod between a first position in which the pivotable platform is lowered toward the floor surface to permit a user to engage first and second pedals and a second position in which the pivotable platform is at least partially raised away from the floor surface to permit transporting the workstation, and
    wherein the pivotable platform comprises an opening configured to receive a fastener of the first mount to retain the pivotable platform in the second position.

2. The apparatus of claim 1 wherein the proximal portion of the second pedal overlaps the distal portion of the first pedal such that a combined depth of the first and second pedals is 200 mm, and wherein a depth of overlap between the proximal portion and the distal portion is at least 12 mm.

3. The apparatus of claim 1 wherein the second angle of the second actuation surface is 14° relative to the floor surface.

4. The apparatus of claim 1 wherein the first angle of the first actuation surface is 7° relative to the floor surface.

5. The apparatus of claim 1 wherein the pivotable platform is mounted to the workstation to facilitate ergonomic operation of the first and second pedals by feet of a user seated in a chair that includes a seat portion positioned at a reclining angle, and wherein the pivotable platform is configured to pivot such that at least one of the first angle of the first actuation surface or the second angle of the second actuation surface generally corresponds to the reclining angle of the seat portion.

6. The apparatus of claim 5 wherein the second angle of the second actuation surface is 14° relative to the seat portion of the chair, and wherein the first angle of the first actuation surface is 7° relative to the seat portion.

7. The apparatus of claim 1 wherein the fastener comprises a spring pin configured to engage with the opening to maintain the pivotable platform in the second position and to disengage from the opening to cause the pivotable platform to pivot to the first position.

8. The apparatus of claim 1 wherein:
    the first mount comprises a first sliding track and the second mount comprises a second sliding track;
    the first and second mounts are configured to be attached to the workstation; and
    the first and second tracks configured to permit forward and backward movement of the first and second mounts.

9. The apparatus of claim 8 wherein the first and second tracks are configured to be received in first and second rails of the workstation.

10. The apparatus of claim 1 wherein the pivotable platform comprises first and second protrusions positioned on respective sides of a bottom portion of the pivotable platform, each of the first and second protrusions comprising an opening housing the rod.

11. The apparatus of claim 10 wherein each of the first and second protrusions comprises a base and a clamp connected to the base.

12. A workstation comprising:
    the foot pedal apparatus of claim 1;
    an input device; and
    hand controllers configured to generate input signals, wherein the pivotable platform is configured to attach to the workstation at a position forward of hands of a user when seated in a chair in front of the workstation and grasping the hand controllers to permit feet of the user to be extended away from the chair for ergonomic operation of the first and second pedals.

13. The workstation of claim 12 wherein the first and second mounts are configured to facilitate positioning the first and second pedals in an ergonomic position in accordance with a user preference.

14. The workstation of claim 12 further comprising at least one additional pedal mounted on the pivotable platform spaced apart from the first and second pedals, and wherein the first and second pedals are mounted on the pivotable platform for accessibility by one foot of the user while the at least one additional pedal is mounted on the pivotable platform for accessibility by another foot of the user.

15. The workstation of claim 12 further comprising:
a third pedal mounted on the pivotable platform and including a third upwardly disposed actuation surface, the third pedal being adjacent to the first pedal and correspondingly oriented; and
a fourth pedal mounted vertically elevated with respect to the third pedal and including a fourth upwardly disposed actuation surface, the fourth pedal being adjacent to the second pedal and correspondingly oriented.

16. The workstation of claim 15 wherein the first, second, third and fourth pedals are mounted closely adjacent on the pivotable platform for accessibility by a foot of the user.

17. The workstation of claim 16 further comprising a barrier disposed between the first and third pedals and a barrier disposed between the second and fourth pedals, the barriers each protruding above the actuation surfaces of the respective pedals.

18. A workstation comprising the foot pedal apparatus of claim 1 wherein the workstation is supported on a wheeled base.

19. A foot pedal apparatus for use with a robotic surgery system workstation, the apparatus comprising:
a first mount configured to be mounted to the workstation;
a second mount configured to be mounted to the workstation;
a pivotable platform extended between the first and second mounts, the pivotable platform comprising a first protrusion and a second protrusion positioned on respective sides of a bottom portion of the pivotable platform, each of the first protrusion and the second protrusion comprising an opening housing a rod;
a first pedal mounted on the pivotable platform and including a first upwardly disposed actuation surface, the first actuation surface positioned at a first angle relative to a floor surface; and
a second pedal mounted vertically elevated with respect to the first pedal and including a second upwardly disposed actuation surface, the second actuation surface positioned at a second angle relative to the floor surface, the second pedal including at least a proximal portion overlapping a distal portion of the first pedal, wherein the pivotable platform is configured to pivot and alter at least one of the first angle of the first actuation surface or the second angle of the second actuation surface relative to the floor surface to facilitate ergonomic operation of the first and second pedals.

20. The apparatus of claim 19 wherein the proximal portion of the second pedal overlaps the distal portion of the first pedal such that a combined depth of the first and second pedals is 200 mm, and wherein a depth of overlap between the proximal portion and the distal portion is at least 12 mm.

21. The apparatus of claim 19 wherein the second angle of the second actuation surface is 14° relative to the floor surface.

22. The apparatus of claim 19 wherein the first angle of the first actuation surface is 7° relative to the floor surface.

23. The apparatus of claim 19 wherein the pivotable platform is mounted to the workstation to facilitate ergonomic operation of the first and second pedals by feet of a user seated in a chair that includes a seat portion positioned at a reclining angle, and wherein the pivotable platform is configured to pivot such that at least one of the first angle of the first actuation surface or the second angle of the second actuation surface generally corresponds to the reclining angle of the seat portion.

24. The apparatus of claim 23 wherein the second angle of the second actuation surface is 14° relative to the seat portion of the chair, and wherein the first angle of the first actuation surface is 7° relative to the seat portion.

25. The apparatus of claim 19 wherein:
the first mount comprises a first sliding track and the second mount comprises a second sliding track;
the first and second mounts are configured to be attached to the workstation; and
the first and second tracks configured to permit forward and backward movement of the first and second mounts.

26. The apparatus of claim 25 wherein the first and second tracks are configured to be received in first and second rails of the workstation.

* * * * *